United States Patent [19]

Hethuin

[11] Patent Number: 5,458,122
[45] Date of Patent: Oct. 17, 1995

[54] SYSTEM FOR WIRELESS TRANSMISSION OF MEDICAL DATA

[75] Inventor: Serge Hethuin, St Remy Les Chevreuses, France

[73] Assignee: Thomson-CSF, Paris, France

[21] Appl. No.: 115,600

[22] Filed: Sep. 3, 1993

[30] Foreign Application Priority Data

Sep. 4, 1992 [FR] France ................... 92 10568

[51] Int. Cl.$^6$ .............................. A61B 5/0402
[52] U.S. Cl. ................... 128/696; 128/901; 128/903
[58] Field of Search ..................... 128/696, 903, 128/902, 901, 904

[56] References Cited

U.S. PATENT DOCUMENTS

| | | | |
|---|---|---|---|
| 3,690,313 | 9/1972 | Weppner et al. ............ | 128/902 |
| 3,902,478 | 9/1975 | Konopasek et al. . | |
| 4,478,224 | 10/1984 | Bailey ................ | 128/901 |
| 4,625,733 | 12/1986 | Säynäjäkangas ............ | 128/903 |
| 4,958,645 | 9/1990 | Cadell et al. . | |

FOREIGN PATENT DOCUMENTS

| | | |
|---|---|---|
| 0347515 | 12/1989 | European Pat. Off. . |
| 675675A5 | 10/1990 | Germany . |
| 90/09143 | 8/1990 | WIPO . |
| 91/16851 | 11/1991 | WIPO . |

*Primary Examiner*—William E. Kamm
*Assistant Examiner*—Scott M. Getzow
*Attorney, Agent, or Firm*—Oblon, Spivak, McClelland, Maier, & Neustadt

[57] ABSTRACT

The system for wireless transmission of medical data comprises a piece of transmission equipment carried by the patient which comprises a unit for differential amplification and band filtering, a unit for rejection of interference noises, particularly the sector and its harmonics, existing in the band of the useful signal, an amplification circuit with automatic gain control and a modulator receiving a carrier frequency, for example microwave at 2.45 GHz and the useful signal, in analog or after a digital conversion and optional processings. The system also comprises a suitable receiving station. The carrier frequency can be either generated in the transmission equipment, or in the receiving station which then transmits the nonmodulated carrier for the transmitters that are associated with it.

16 Claims, 5 Drawing Sheets

SYSTEM FOR WIRELESS TRANSMISSION OF MEDICAL DATA

BACKGROUND OF THE INVENTION

1. Field of the Invention

The invention relates to the field of medical electronics and, more particularly, has as its object a system for wireless transmission of medical data.

2. Discussion of the Background

Certain medical examinations use the detection of electrical fields. This is particularly the case in electrocardiography.

Conventionally, to perform an electrocardiogram, electrodes are placed at precise points of the body and the voltages detected between these points are amplified in a differential amplifier with suitable characteristics, followed by a graphic recorder. In units used for monitoring, the graphic recorder is replaced or completed by an oscilloscope. The diagnostic value of the electrocardiogram or "EKG" is considerable: changes of the waveforms recorded are very significant.

Conventionally, for complete examinations intended to characterize completely the electric activity of the heart in 3 dimensions, 3 characterization signals are formed from 10 electrodes: 3 electrodes called "principal," D, G, P; 1 reference electrode; and 6 electrodes called "precordial." The patients are lying down and wires connect the electrodes placed on the body to the electronic circuits of the electrocardiograph. This connection is, for example, performed as follows: 10 elemental leads are connected to 10 electrodes placed at the points required for the examination. These 10 leads are connected to a concentrator by "banana"-type connectors and a multiconductor shielded cable connects the concentrator to the recorder via a DIN connector. This structure is heavy, expensive, constraining for the patient and its safety of operation is not even completely assured since breaks or anomalies in the wire connections, particularly when the central core of a lead is damaged, produce noise and artifacts, even a disappearance of the corresponding signal.

Moreover, if the lying down position is suitable for some measurements, it is not suitable for measurements during stress tests. Now these examinations are very advantageous in following the variations of the EKG signals as a function of stress. In the standard systems, the patient is a "home trainer" and the problems of vibration, of sudation accentuate the deficiencies of the leads. In addition, the equipment, which is in the way, carried by the patient restricts him during his effort.

Other pieces of equipment, of a portable type, are provided to record the EKG signals on a magnetic tape recorder carried on the belt and connected by leads to the electrodes. Such pieces of equipment that can be used on the outside for monitoring patients throughout their activity can make it possible to record all the signals for 12H or 24H to find anomalies, connected with the activity, that are undetectable during office examinations. Such a piece of equipment does not make possible a monitoring of the patient in real time but only in delayed time after reading, optionally speeded up, of the tape.

A piece of test equipment is also known that is particularly intended for athletes in particular to improve their training. This piece of equipment comprises a transmitter placed on the chest of the athlete which detects the overshootings in relation to a threshold ("R" points of the EKG PQRST complex signal), and wirelessly transmits pulses corresponding to these points to a receiving microcomputer carried on the wrist. This wireless transmission is performed according to the principle of the magnetic field; water, clothes or the wet body do not disturb the transmission. The piece of equipment makes it possible to record the cardiac frequency according to a sampling at a pace of 5, 15 or 60 sec, for example for a total period that is a function of the storage capacities.

As the short description given above shows, this equipment makes it possible to follow only the cardiac frequency, and the use of the results can be realized in real time only by the athlete and only to the extent that a display can be provided on the receiver. As in the piece of equipment described previously, such a piece of equipment does not permit real-time following by a medical team.

SUMMARY OF THE INVENTION

The invention has as its object a system for transmission of medical data which does not exhibit the drawbacks of the systems using wire connections and which makes it possible to have the EKG signals of at least one patient being monitored by a medical team followed in real time and optionally remotely without limitations of the parameters observed. In the most improved embodiments, it is possible to follow fifty patients remotely.

According to the invention, a system for transmission of medical data, without wire for the transmission of characteristic electric signals resulting from an electric field between electrodes placed on the body of a patient, is characterized in that it comprises a piece of transmission equipment to be held on the body of the patient by removable means, connected to two electrodes and comprising a differential amplification and band filtering unit also connected to a reference electrode to filter the band of the useful signal while rejecting the common mode, a unit for selective rejection of the frequency of the sector and of its harmonics in the band of the useful signal, and a modulator of a carrier at the transmission frequency, by the useful signal.

BRIEF DESCRIPTION OF THE DRAWINGS

The invention will be better understood and other characteristics will come out on reading the following description, with reference to the accompanying figures.

DETAILED DESCRIPTION OF THE PREFERRED EMBODIMENT

As indicated above, according to the invention, the transmission of medical data, particularly the data for characterization of the electrical activity of the heart, is performed no longer by wire but by transmission of the electrical signals on electromagnetic carrier waves to avoid all the problems connected with the connector technology. Nevertheless, it is essential for the use of such transmissions to take into account the demands for safety required for this type of equipment and the constraints connected with the environment in which these systems must operate. The various wavebands, VLF, UHF, SHF, IR will be able to be used. They each have advantages but also constraints of use. The bands to transmit must be suitable for the associated carrier wave. Finally, it is essential so that a complete real-time monitoring can be performed, that the EKG complex signal can be transmitted in its entirety. A few reminders on the characteristics of this signal making it possible to better understand the type of constraints to be considered are given hereafter. The electrical signals picked up between electrodes have an amplitude on the order of a millivolt and a band on the order of 0.5 Hz to 500 Hz (frequency of the rising edge of the "R" pulse). These useful signals must be separated from the signals in the sector frequency, (50 Hz in Europe), and from its harmonics, which are specifically in the band of the useful signal, by filtering but without this filtering affecting the useful signals.

On the other hand, to obtain the necessary safety in case of disturbance, the preferred embodiments of the system according to the invention transmit the data by frequency or phase modulation and in certain cases make it possible to use error correction codes.

Finally, the wireless transmission has the considerable advantage that it makes it possible for a single medical team to monitor several patients, each of them carrying a transmitter that transmits the EKG signals to the monitoring center. But to obtain this functionality, it is essential that the disturbances between pieces of equipment of the same type be minimized, which implies that the data can easily be separated, i.e., be transmitted on carriers of different frequencies (selection of the FDMA type channel) if an analog modulation is used. In a digital modulation, it is possible indiscriminately to use a separation by carriers (FDMA type) or a separation by orthogonal PN codes (CDMA type).

Figure 1:
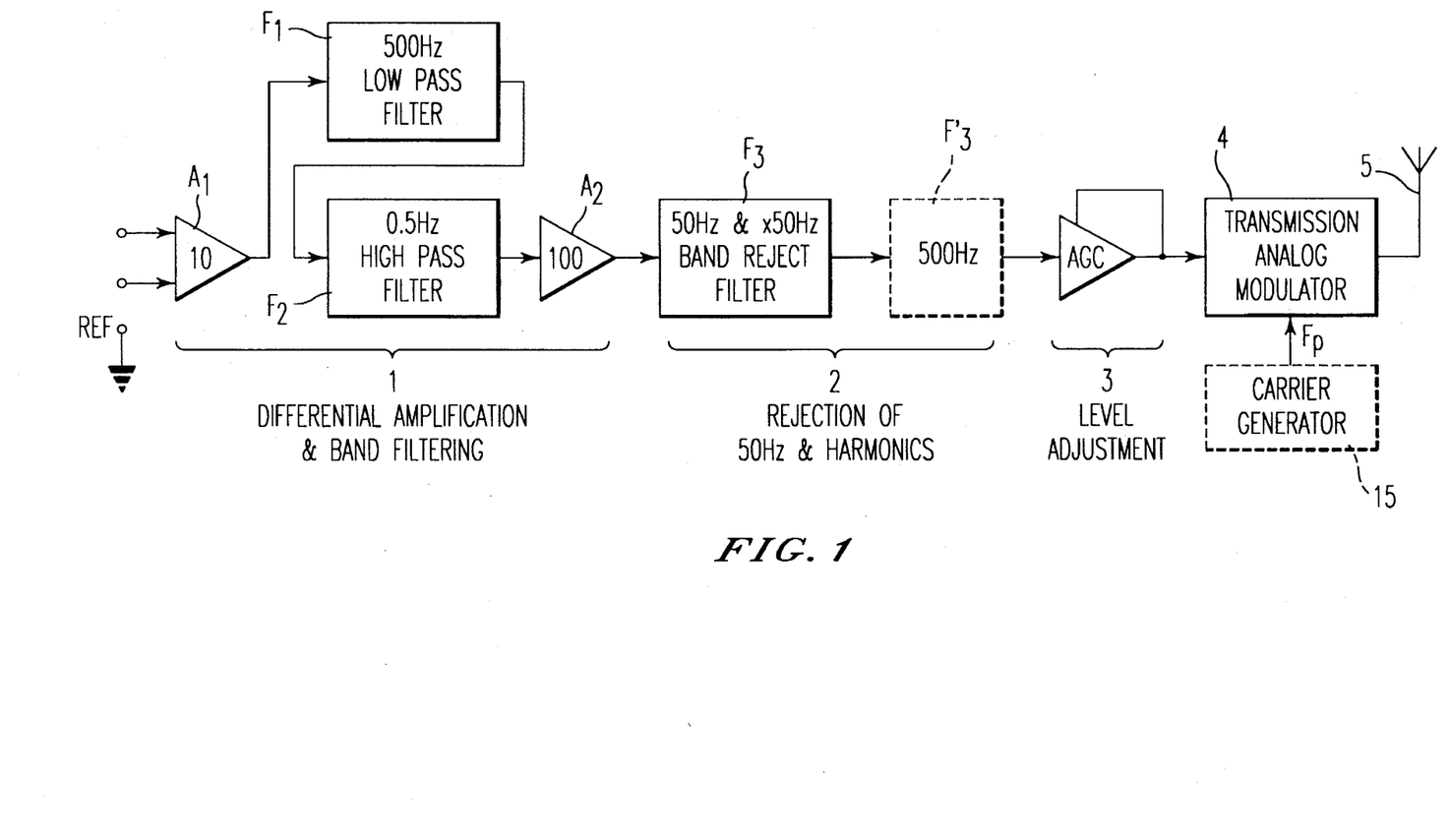
FIG. 1 illustrates in a first embodiment the transmission equipment of the system according to the invention, in an analog mode.

FIG. 1 illustrates the transmission equipment according to the invention in it simplest embodiment.

Two electrodes, namely $E_1$ and $E_2$ between which it is desired to follow the variation in electric voltage, are connected to two inputs of a differential amplification stage $A_1$, reference electrode Ref giving the ground potential of the amplifier. The gain of this stage is on the order of 10. A low-pass filter $F_1$ whose cutoff frequency is on the order of 500 Hz is placed at the output of this amplification stage. A high-pass filter $F_2$ whose cutoff frequency is on the order of 0.5 Hz is connected to the output of the low-pass filter and an amplifier $A_2$ having a gain on the order of 100 is placed at its output.

This first unit, 1, for differential amplification and band filtering, makes it possible to reject the common mode, i.e., a large part of the interference noises picked up simultaneously by the two carrying electrodes, and particularly of the 50 Hz sector, and transmits only the band of the useful signal, between 0.5 Hz and 500 Hz. However, interference noises exist in the band at 50 Hz and at the harmonics of 50 Hz. For this reason a second unit of circuits 2 is then provided to eliminate as completely as possible these interference noises and only these interference noises. It comprises a band-reject filter $F_3$ exhibiting a very considerable attenuation in a 0.4 Hz narrow band, around 50 Hz and the harmonics. To obtain these characteristics, the preferred embodiment of this filter $F_3$ is a multiharmonic noise suppressor with n paths, n being chosen equal for example to 8. In this case, a low-pass filter $F'_3$ (illustrated in broken lines) with a 500 Hz cutoff frequency is provided to cut off the frequencies higher than 500 Hz generated by the noise suppressor.

The third unit, 3, is an amplifier circuit with automatic gain control so that the signal applied to transmission circuits 4 which follow have suitable dynamics. In this embodiment, the simplest of the transmission equipment of the system according to the invention, the transmission circuits comprise a modulator, by phase or by frequency preferably, of a carrier $F_p$ at the transmission frequency, for example in the 2 GHz band, delivering the modulated carrier, applied to the transmission antenna, 5.

This transmission equipment is carried by the patient and can easily be contained in a small box held on the chest of the person to be monitored, for example, by a belt, the two electrodes carried by the belt being connected to terminals provided on the box. This embodiment in which the equipment is "analog," which has the advantage of simplicity and compactness, exhibits however the drawback of being sensitive to disturbances by exterior transmissions and to disturbances between pieces of equipment of the same type, which as indicated above will have to transmit at different frequencies.

Figure 2:
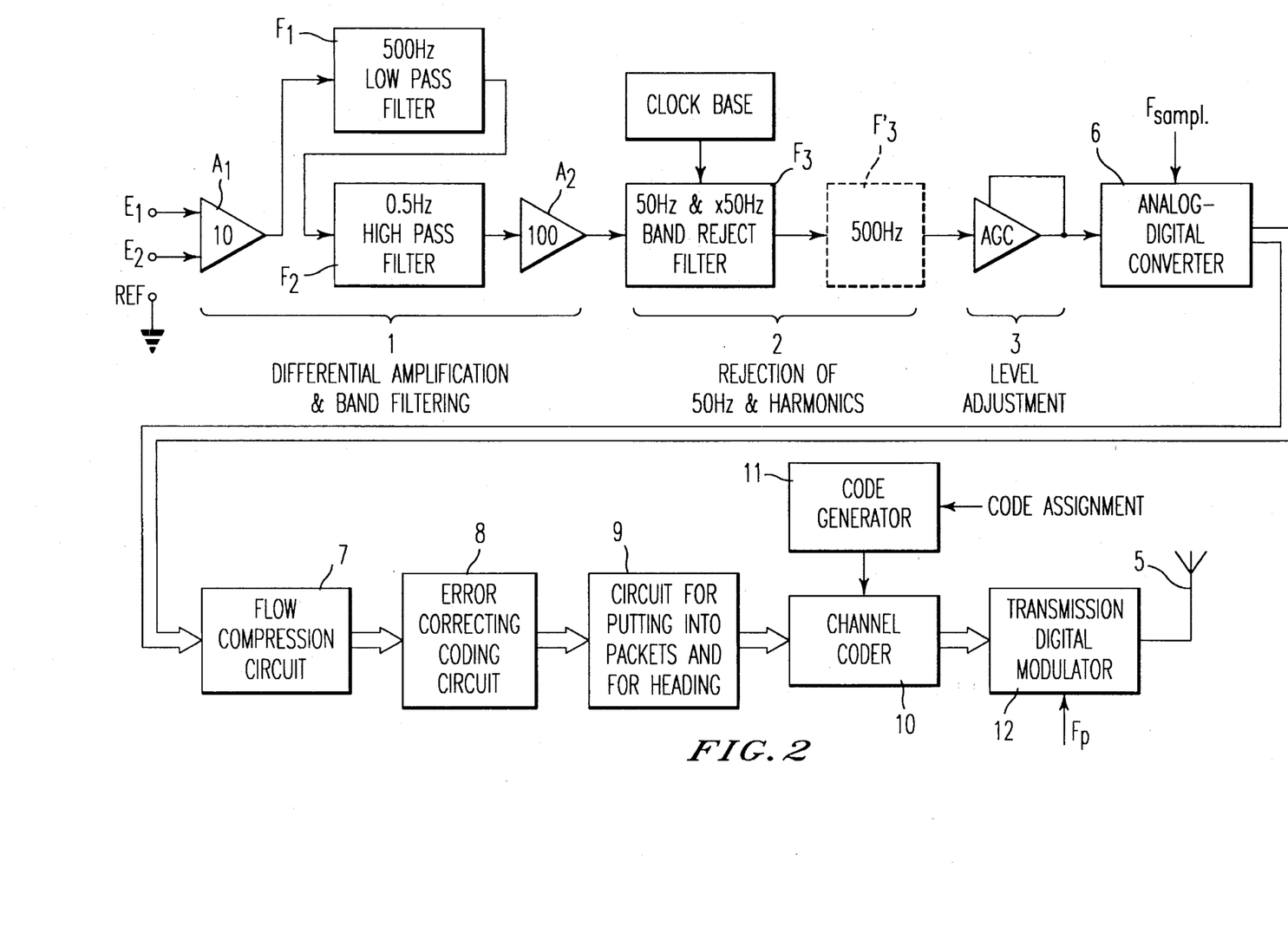
FIG. 2 illustrates a second embodiment of the transmission equipment, in a digital mode.

FIG. 2 illustrates a second embodiment of a piece of equipment according to the invention in which the modulation of the carrier is performed digitally. It comprises as the first embodiment, units 1, for differential amplification and band filtering, 2, for rejection of the 50 Hz sector and its harmonics and 3 for automatic gain control.

But the EKG signal to be transmitted is then digitized by means of an analog-digital converter, 6, on 12 bits for example, controlled at sampling frequency $F_{ech}$, for example 1 kHz. A flow compression circuit 7 connected to the output of the converter makes it possible to reduce the flow from 12 kbits/sec to 1 kbit/sec.

The equipment then comprises, in series, an error correcting coding circuit 8, for correction on receipt of the data received, by RS (Reed Solomon) or BCH (Binary Coding Hamming) type code, then a formation circuit 9 for putting the data in packets with heading generation for the synchronization of the messages, and finally a channel coder 10 by a pseudorandom PN coding, of "GOLD" OR "KASAMI" type. The flow then goes from 1 kbit/sec to 256 kbit/sec. The KASAMI type code makes it possible to define N=16 orthogonal channels with a code length equal to 17×15=255 elements. To do this, a code generator 11 controls channel coding circuit 10. The code pertaining to the transmitter being determined by keys making it possible to assign a particular code to each transmitter, in a definitive or reprogrammable way depending on the applications.

The coded digital signal is then applied to a digital modulator 11 which, furthermore, receives the carrier frequency to be modulated $F_p$, and transmits the modulated carrier to transmission antenna 5.

The embodiment specifically described above comprises a circuit for automatic gain control on the analog signal before digitizing. This circuit is not essential if the dynamics of the converter are sufficient. In this case, the AGC function can be performed entirely digitally, there is then no longer any amplification with automatic gain control, or digitally only for the production of the control, the control signal produced from the converter output signal is then used to control a variable gain amplifier located before the converter.

Also, the embodiment described above comprises a channel coder (10) and the associated code generator. For a system requiring only one simplex communication channel, a transmitter connected to a short range receiver, these elements can be eliminated.

The equipment in the digital modulation version described above is very efficient since it makes it possible to use all the digital techniques for correction of errors and for separation of the known channels. But its level of sophistication can be very great particularly for applications where the least cost is an essential aspect.

Figure 3:
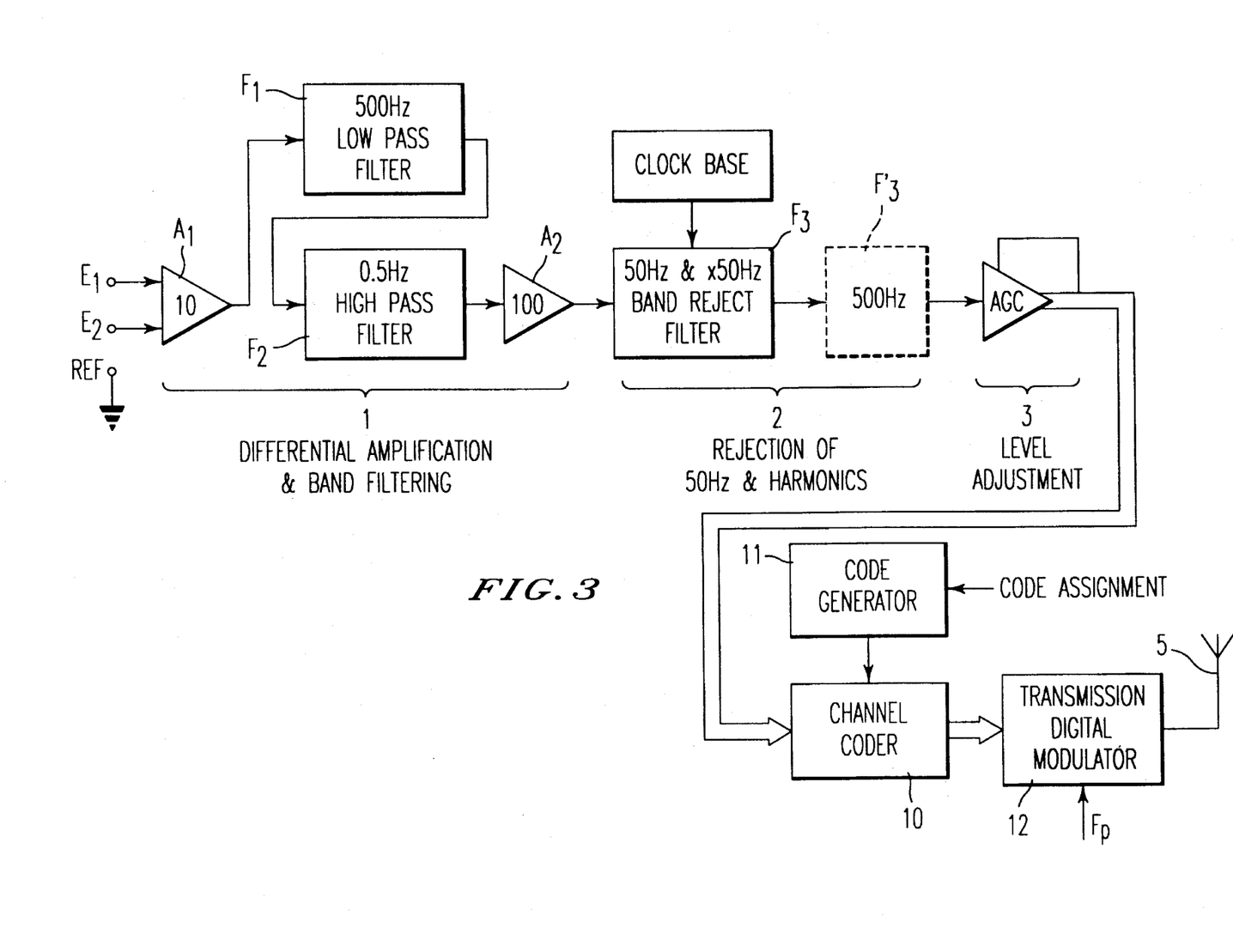
FIG. 3 illustrates a third embodiment of the transmission equipment, in a mode known as "semi-digital."

The third embodiment of the invention illustrated in FIG. 3 is an effective compromise between the simplest embodiment described in reference to FIG. 1 and the very sophisticated digital embodiment described in reference to FIG. 2.

The equipment comprises, as before, unit 1 for differential amplification and band filtering, unit 2 for rejection of the 50 Hz and its harmonics, unit 3 for amplification with automatic gain control, but instead of sampling the analog signal to obtain a digitized signal which after processing modulates a carrier $F_p$, the EKG analog signal is directly modulated by a circuit 10 for channel coding by a pseudorandom PN code selected among several orthogonal codes, to make possible on receipt to distinguish the signal transmitted by this transmitter from an analog signal transmitted by a neighboring transmitter.

Figure 4:
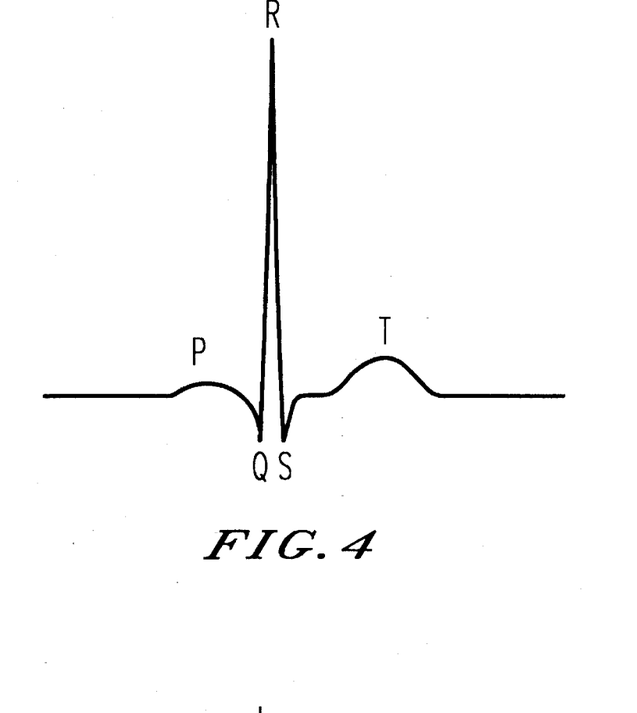
FIG. 4 represents a period of the EKG signal.
Figure 5:
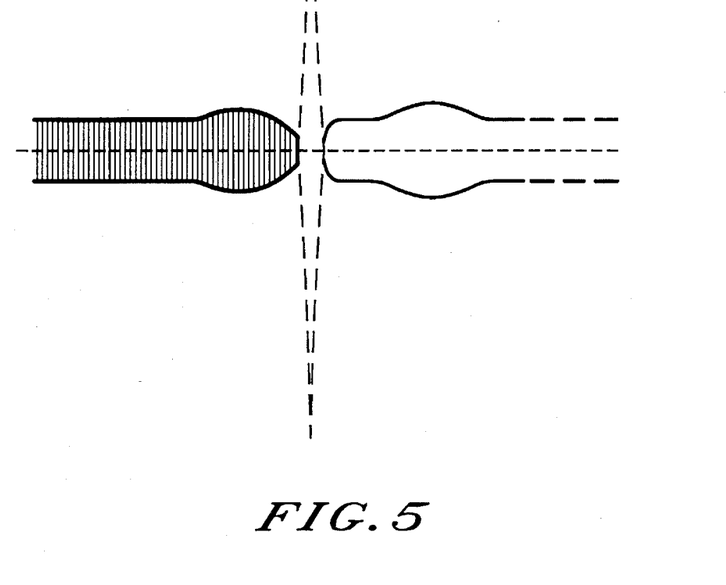
FIG. 5 illustrates the signal coming from the channel coder in the semi-digital embodiment of the transmission equipment.

FIGS. 4 and 5 make it possible to illustrate this modulation.

FIG. 4 illustrates the EKG signal with its characteristic PQRST points and FIG. 5 illustrates the signal coded after channel coding by pseudorandom code. The cyclic code peculiar to the channel is repeated each millisecond, or nearly 1000 times over a period on the order of 1 sec of the EKG wave. As described above, for a frequency of change of state of the code of 256 kHz, the length of the code is L=255 elements obtained with a code on 8 bits to which is added an elementary period for resetting the generator to zero, which makes it possible to generate at most 16 orthogonal channels by KASAMI code.

The signal thus coded is directly applied to modulator 11 of carrier frequency $F_p$. Thus, as before, nearby communications are differentiated by the codes assigned to each of them even if their carriers are identical (Technique known as "CDMA").

Thus, a version of the equipment is obtained that is effectively protected and of a complexity clearly less than that of the digital version described above.

Of course, this version does not allow introducing an error correcting coding, but however makes possible a weighting of the results obtained as a function of the correlation maximums.

For the first two embodiments of the transmission equipment according to the invention, the corresponding receiving station comprises means for receiving, for demodulating and, for the digital version, for decoding, and for restoring the EKG analog signal which are standard. For managing several transmitters, it also comprises means for separating the necessary channels.

For the third embodiment of the transmission equipment, semi-digital, the receiving equipment is adapted.

Restoring the signal on receipt is done by synchronization on the code, i.e., from a signal "sample" at the 1 kHz frequency. Actually, it is necessary to acquire the synchronization, i.e., to mark the moments where the expected code is present, by correlation with the code reference and to subsample the signal thus constructed by taking the successive samples corresponding to the successive maximums of the correlation signal: the restored signal is a signal at the rate of 1 kHz.

Figure 6:
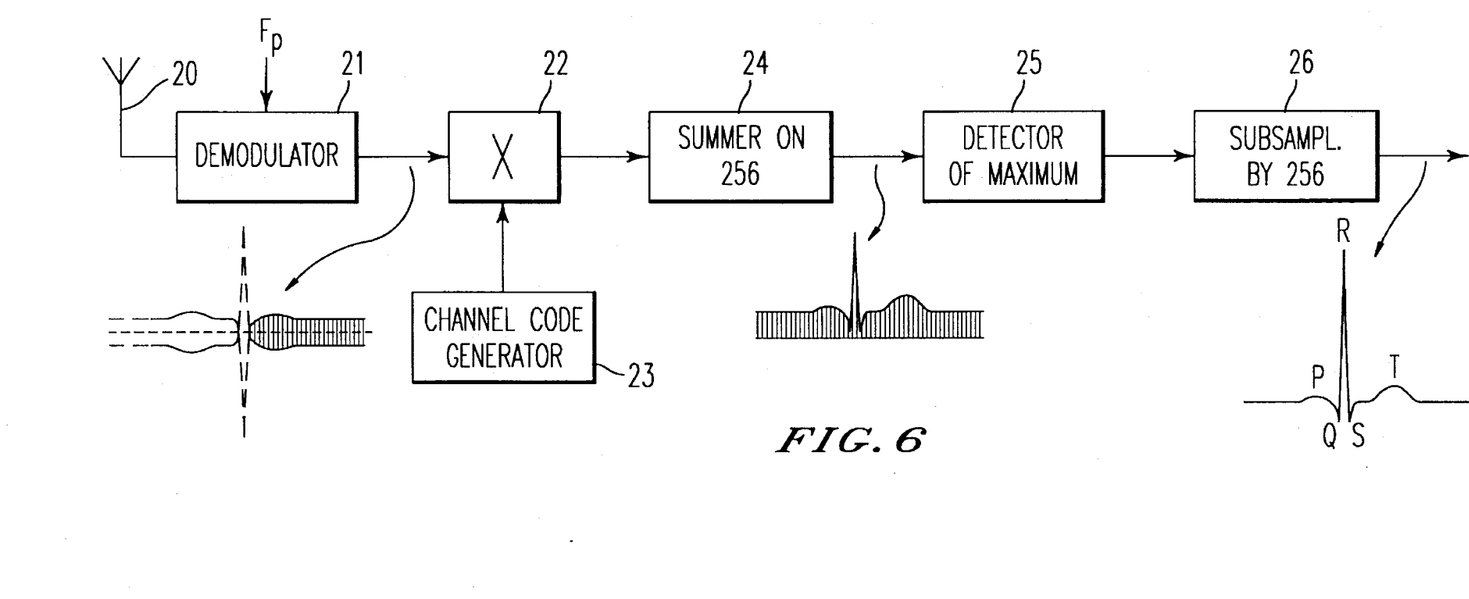
FIG. 6 illustrates the unconventional portion of the receiving equipment associated with a semi-digital embodiment of the transmission equipment.

The block diagram of the receiver associated with the transmitter to form the system according to the invention is illustrated in FIG. 6 where there have also been illustrated the three point signals of the receiver; the signal received on receiving antenna 20 is the carrier modulated by the coded EKG signal. After demodulation and digitization of the quadrature paths I and Q in a demodulator 21 receiving carrier frequency $F_p$ and corresponding to the modulator used in the transmitter, this signal is applied to an operator 22 which furthermore receives the code assigned to the channel corresponding to the transmitter to be monitored of a code generator 23. A summer 24 on 256 elements, i.e., the length of code, then makes it possible in a detector of maximums 25 to detect maximums that correspond to a synchronization between the channel code and the successive signal samples at the input of the operator. The envelope of these maximums obtained after subsampling by 256 in a circuit 26 is the EKG signal, restored PQRST.

In the above-described embodiments of the transmitter, it was not specified how the carrier frequency was generated. In a standard way it can be derived from a carrier generator 15 located in the transmitter, as illustrated in broken lines in FIG. 1. But, in another embodiment, the invention could, after production of the modulation signal, use a microwave transmission system in which the monitoring station S, to which the data produced in the equipment carried by the patient are intended, transmits for this equipment a microwave interrogation carrier wave $F_p$, at 2.45 GHz for example.

The equipment carried by the patient $P_1$, $P_2$. . . $P_4$ comprises a card for modulating the received wave by the data to be transmitted before return to the station.

The invention, with a very wide field of application, can be adapted to the various applications intended. Actually, for a piece of equipment intended for a cardiology office, a unidirectional (SIMPLEX point to point) communication from the patient to a receiver located a few meters away for examination or diagnosis by the specialist is enough. The pieces of information to be transmitted are the principal electrode EKG signals ($E_1$, $E_2$, $E_3$/Reference). These pieces of information can be transmitted sequentially. The receiver is coupled to a plotting table (analog or digital) and/or to a recorder (analog or digital). Each patient/receiver communication is selective and corresponds to a different examination room. The number of necessary simultaneous communications is at most on the order of 10. The examination period is on average 10 min, the desired operating radius is on the order of a day (the recharging of the batteries is possible at night). A comparable use can be found at the veterinarian's for cardiology examinations of race horses, in particular.

For a cardiology clinic or a convalescent home, the conditions are a bit different: The equipment makes possible a unidirectional (SIMPLEX point to point) communication from the patient monitored to a receiver

- either located a few meters away in the patient's room. The receiver is then connected to a central recording device (optionally equipped with a self-diagnosis system) by two-wire communication
- or located at a NODAL point and receiving all the data transmitted by the different communications: either directly (the range having to be very large) or indirectly by means of relay flags.

OTHER PUBLICATIONS

The pieces of information to be transmitted are the principal electrode EKG signals ($E_1$, $E_2$, $E_3$/reference). These pieces of information can be transmitted sequentially. The central receiver is coupled to a plotting table (analog or digital) and/or to a recorder (analog or digital). The short range receiver corresponds to an in-room use while the central (nodal) receiver makes possible a monitoring of the patient regardless of his position in the clinic. Each patient/receiver communication is selective. The number of simultaneous communications can be greater than 10. A bidirectional (DUPLEX) communication can also be used; the return then making it possible to transmit a vocal or sound alarm (for order to rest, return to the room for examination . . . ). In the absence of this, an alarm method of the "pager" type can be very useful.

OTHER PUBLICATIONS

The applications described above are not limiting. The equipment according to the invention can also be used in sports rooms.

What is claimed as new and desired to be secured by Letters Patent of the United States is:

1. A system for transmitting medical data, comprising:
   at least two electrodes to be placed on a body of a patient for generating an electrical signal;
   a first unit for receiving the electrical signal from the at least two electrodes and for differential amplification and band-pass filtering of the electrical signal to reject a common mode;
   a second unit for receiving the electrical signal differentially amplified and band-pass filtered from the first unit and for selectively rejecting a frequency of a sector and harmonics of the sector of the electrical signal, to generate an electrical transmission signal; and
   a modulator for receiving the electrical transmission signal from the second unit and for modulating the electrical transmission signal by a transmission frequency carrier; and
   an antenna for transmitting the modulated electrical transmission signal.

2. The system according to claim 1, wherein the modulator is a phase or frequency analog modulator, and the system further comprises an amplification circuit with automatic gain control located between the second unit and the modulator, and the modulator modulates the electrical transmission signal by the transmission frequency carrier in baseband.

3. The system according to claim 2, further comprising:
   a channel coding circuit connected between the second unit and the modulator; and
   a code generator connected to the channel coding circuit and which generates a code associated with a communication channel, to code the electrical transmission signal before transmission to the modulator.

4. The system according to claim 11, wherein the modulator is a digital modulator, and the system further comprises a chain for conversion and for digital processing of the electrical transmission signal in baseband to generate a digital electrical transmission signal, the modulator modulating the digital electrical transmission signal by the transmission frequency carrier.

5. The system according to claim 4, wherein the chain for conversion and for digital processing comprises, in series, a flow compression circuit, an error correcting coding circuit, and a circuit for formatting data to be transmitted.

6. The system according to claim 5, further comprising:
   a channel coding circuit connected between the second unit and the modulator; and
   a code generator connected to the channel coding circuit for generating a code associated with a communication, to code the electrical transmission signal before transmission to the modulator.

7. The system according to claim 6, wherein the code generator uses orthogonal pseudorandom codes of the GOLD or KASAMI type to define a number N of channels that can be separated using the same transmission frequency carrier.

8. The system according to claim 5, wherein the transmission frequency carrier is generated by a carrier frequency generator.

9. The system according to claim 1, further comprising a receiving station comprising a demodulator and a chain for processing the demodulated signal for the restoration of the electrical transmission signal.

10. The system according to claim 9, further comprising a channel coder connected between the second unit and the modulator and including an automatic gain control;
    and wherein the chain for processing of the demodulated signal comprises an operator connected to an output of the demodulator and to an output of a channel code generator.

11. A system for transmitting medical data, comprising:
    at least two electrodes to be placed on a body of a patient for generating an electrical signal;
    a first unit for receiving the electrical signal from the at least two electrodes and for differential amplification and band-pass filtering of the electrical signal to reject a common mode;
    a second unit for receiving the electrical signal differentially amplified and band-pass filtered from the first unit and for selectively rejecting a frequency of a sector and harmonics of the sector of the electrical signal, to generate an electrical transmission signal;
    a chain for conversion and for digital processing of the electrical transmission signal in baseband to generate a digital electrical transmission signal, wherein the chain for conversion and for digital processing comprises, in series, a flow compression circuit, an error correcting coding circuit, and a circuit for formatting data to be transmitted;
    a digital modulator for receiving the electrical transmission signal from the chain for conversion and for digital processing and for modulating the electrical transmission signal by a transmission frequency carrier; and
    an antenna for transmitting the modulated electrical transmission signal.

12. The system according to claim 11, further comprising:
    a channel coding circuit connected between the second unit and the modulator; and
    a code generator connected to the channel coding circuit for generating a code associated with a communication, to code the electrical transmission signal before transmission to the modulator.

13. The system according to claim 12, wherein the code generator uses orthogonal pseudorandom codes of the GOLD or KASAMI type to define a number N of channels that can be separated using the same transmission frequency carrier.

14. The system according to claim 11, further comprising a receiving station comprising a demodulator and a chain for processing the demodulated signal for the restoration of the electrical transmission signal.

15. The system according to claim 14, further comprising a channel coder connected between the second unit and the modulator and including an automatic gain control;
and wherein the chain for processing of the demodulated signal comprises an operator connected to an output of the demodulator and to an output of a channel code generator.

16. The system according to claim 11, wherein the transmission frequency carrier is generated by a carrier frequency generator.

* * * * *